United States Patent [19]

Johansson et al.

[11] Patent Number: 4,632,122
[45] Date of Patent: Dec. 30, 1986

[54] METHOD AND APPARATUS FOR CONDUCTING BRAIN FUNCTION DIAGNOSTIC TEST

[76] Inventors: Nils E. Johansson, 18 Pine Rd., Bedford Hills, N.Y. 10507; Emin Eralp, 11 Eastern Ave., Ossining, N.Y. 10562; Turan M. Itil, 49 Tweed Blvd., Nyack, N.Y. 10960

[21] Appl. No.: 726,729

[22] Filed: Apr. 24, 1985

[51] Int. Cl.$^4$ ............................................. A61B 5/04
[52] U.S. Cl. .................................... 128/644; 128/731
[58] Field of Search ................ 128/639, 644, 731, 791

[56] References Cited

U.S. PATENT DOCUMENTS

| | | | |
|---|---|---|---|
| 2,549,836 | 4/1951 | McIntyre et al. | 128/644 |
| 3,508,541 | 10/1967 | Westbrook et al. | 128/644 |
| 3,602,216 | 8/1971 | Moe, Jr. | 128/640 |
| 3,998,213 | 12/1976 | Price | 128/644 |
| 4,166,457 | 10/1979 | Jacobsen et al. | 128/639 |

FOREIGN PATENT DOCUMENTS 2124704 11/1972 Fed. Rep. of Germany ...... 128/644

Primary Examiner—Kyle L. Howell
Assistant Examiner—Randy Citrin
Attorney, Agent, or Firm—Evelyn M. Sommer

[57] ABSTRACT

Method and apparatus are provided for use in conducting an electroencephalographic (EEG) test where the apparatus includes a headset suitable for placement on the head of a subject to be tested. A plurality of electrodes are mounted on the headset at pre-determined positions about the headset. The electrodes are preferably mounted to the headset by the use of a resilient material, preferably a resilient wire or plastic mesh which is bonded to both the electrode assembly and to the headset.

Each of the electrode assemblies include a separate air cylinder for displacing the electrode in the direction of the subject's head upon the application of additional air pressure into the cylinder. A bellows arrangement is provided within each air cylinder for effecting displacement of the electrode.

Means are further provided for dispensing a predetermined amount of an electrolytic material from an external source of electrolyte, through the electrode, to the point of contact between the electrode and the subject's head.

13 Claims, 4 Drawing Figures

METHOD AND APPARATUS FOR CONDUCTING BRAIN FUNCTION DIAGNOSTIC TEST

BACKGROUND OF THE INVENTION

The present invention relates generally to method and apparatus for conducting a brain function diagnostic test and, more particularly, to such method and apparatus which can be used to accurately and repeatedly measure a subject's brain waves during electroencephalography.

An electroencephalograph (EEG) is a clinical, multi-channel instrument used to measure and display the brain waves of a subject. The subject's brain waves are monitored in such an EEG by the use of a number of individual electrodes which are attached to the scalp of the subject in a predetermined pattern or montage which is well known in the art. The electrical activity (brain waves) generated by the subject's brain are detected by these electrodes and transmitted to external monitoring devices where they are amplified and displayed for viewing and diagnostic interpretation.

In the early years of EEG testing, the brain waves were displayed using a multichannel recorder with each trace made by a galvanometer-type pen motor. More recently, however, the EEG systems employ a microcomputer into which the brain waves are fed for analysis and display on the computer's accompanying CRT. The computer automatically records, analyzes and artifacts the EEG and prepares a detailed report with the tracing of the EEG. Through the use of the computer's analysis of the brain waves, it is now possible to graphically "map" the brain on the computer's CRT to check for abnormalities relative to an appropriate reference data base.

EEG testing is used not only to detect abnormalities in brain function but, in addition, the therapeutic monitoring of central nervous system (CNS)-effective drugs such as, for example, anti-epileptics, cerebrovascular compounds, psychotropics, etc. EEG testing has also been used clinically to determine the CNS toxicity of peripheral drugs such as cardiovascular drugs, antidepressants, anxiolytics, antihistamines and analgesics; to select the right psychotropic for a particular patient; and to determine the development of a progressive cerebral illness by repetitive quantitive EEG testing.

In research, EEG testing has been used to establish quantitative CNS effects of drugs after single or multiple doses, for classifying psychotropic properties of drugs; for predicting the "therapeutic window" of psychotropics; and for determining the potency of CNS-effective drugs and determining appropriate dose levels.

Representative of current EEG systems include those systems described, for example, in U.S. Pat. Nos. 3,518,986 which issued on July 7, 1970 to T. C. Woods et al. for Patient Monitoring Safety System; 3,859,988 which issued on Jan. 14, 1975 to C. C. Lencioni, Jr. for Open Lead Testing System for EEG; 4,202,352 which issued on May 13, 1980 to L. B. Smith et al.; 4,213,465 which issued on July 22, 1980 to G. Renheim for Electroencephalograph; 4,214,591 which issued on July 29, 1980 to K. Sato et al. for Brain Wave Analyzing System and Method; 4,235,511 which issued on Dec. 2, 1980 to P. J. Loeb for Electroencephalograph; Re. 30,502 which issued on Feb. 3, 1981 to C. C. Lencioni, Jr. for Open Lead Testing System for EEG; 4,409,987 which issued on Oct. 18, 1983 to R. A. McIntyre for Electroencephalograph; 4,411,273 which issued to E. R. John on Oct. 25, 1983 for System and Method for Electrode Pair Derivations in Electroencephalography; and 4,424,816 which issued on Jan. 10, 1984 to A. S. Callahan et al. For Neurological Monitoring Device Test Circuitry.

Despite the sophistication of current EEG testing systems and their related computer hardware and software, the weakest link in all of these systems is the placement and securing of the individual electrodes to the subject's scalp. Nineteen individual electrodes must be located and specifically placed on a subject's scalp and good electrical contact must be established between the electrode and the subject's scalp. Current practice utilizes highly conductive, miniature "cup" shaped electrodes which are fastened to the subject's scalp by means of an adhesive type electrically conductive paste or cream. Placement of such electrodes is determined based on head measurements taken by the technician conducting the test in accordance with the International 10–20 system.

Examples of such prior art electrodes include those electrodes which are described in U.S. Pat. Nos. 2,872,926 which issued on Feb. 10, 1959 to J. E. Alderman for Electroencephalographic Electrode; 3,151,619 which issued on Oct. 6, 1964 to G. H. Sullivan for Electrode for Electromedical Equipment; 3,170,459 which issued on Feb. 23, 1965 to C. G. Phipps et al. for Bio-Medical Instrumentation Electrode; 3,187,745 which issued on June 8, 1965 to J. N. Baum et al. for Electrodes; 3,295,515 which issued on Jan. 3, 1967 to A. R. Kahn for Electrode Assembly; 3,469,577 which issued on Sept. 30, 1969 to J. A. R. Kater for Scalp Contacting Bioelectrode; 3,528,408 which issued on Sept. 15, 1970 to B. Opperman for Chemical Adhesive Electrode; 3,580,239 which issued on May 25, 1971 to H. Watanabe et al. for Method and Apparatus for In Vivo Potentiometric Measurements; 3,602,216 which issued on Aug. 31, 1971 to L. H. Moe, Jr. for Paste Dispensing Body Electrode; 3,623,479 which issued on Nov. 30, 1971 to C. C. Day for ECG Electrode with Partition; 3,669,110 which issued on June 13, 1972 to G. M. Low et al. for Compressible Biomedical Electrode; 4,033,334 which issued on July 5, 1977 to J. C. Fletcher et al. for Snap-In Compressible Biomedical Electrode; and 4,051,842 which issued on Oct. 4, 1977 to P. M. Michael et al. for Electrode and Interfacing Pad for Electrical Physiological Systems.

As a review of these patents will demonstrate, the state of the art relative to electrode design and placement has not advanced nearly as far as that of the related hardware and software used in analyzing the EEG results. Location and placement of the electrodes remains still a trial and error technique. Placement and securing of the 19 electrodes to the subject's scalp is a cumbersome, messy and time consuming method which requires a degree of training. The amount of time required to properly locate and connect the electrodes at nineteen different locations about the subject's scalp determined in accordance with the International 10–20 system can be substantial, often taking as long as thirty to forty-five minutes.

The chances of locating the electrodes in exactly the same positions on the scalp during repetitive testing is difficult, problematic and highly unlikely, thus rendering the reliability of results from repetitive tests somewhat suspect. Moreover, the chances of obtaining and maintaining good electrical contact with the scalp at all nineteen locations can prove difficult due to the differences in skull size and shape and the amount and texture of the hair of different subjects.

Against the foregoing background, it is a primary objective of the present invention to provide a headset unit which includes the plurality of electrodes required to conduct an EEG test.

It is another objective of the present invention to provide such a headset which is adapted to locate and securely place said plurality of electrodes against the scalp of a subject undergoing such an EEG test.

It is still another objective of the present invention to provide such a headset which is able to repeatably locate and place the electrodes at substantially the same location on the subject's scalp in future testing.

It is yet another objective of the present invention to provide such a headset which is adapted to automatically introduce a conductive material between the electrode and the scalp.

It is still yet another objective of the present invention to provide such a headset where the electrodes can automatically adjust to accommodate subjects with scalps of different sizes and shapes.

It is still another objective of the present invention to provide such a headset which is adapted to provide a uniform force to the electrode independent of its positioning relative to the others.

It is yet still another objective of the present invention to provide such a headset which will afford the utilization of an electrolyte in the form of a water soluble gel rather than a sticky paste which can only be removed with great difficulty.

SUMMARY OF THE INVENTION

To the accomplishments of the foregoing objects and advantages, the present invention, in brief summary, comprises method and apparatus for use in conducting an electroencephalographic (EEG) test where the apparatus includes a headset suitable for placement on the head of a subject to be tested. A plurality of electrodes are mounted on the headset at pre-determined positions about the headset. The electrodes are preferably mounted to the headset by the use of a resilient material, preferably a resilient mesh such as a plastic mesh, which is bonded or otherwise fastened to both the electrode assembly and to the headset.

Each of the electrode assemblies includes a separate air bellows for displacing the electrode in the direction of the subject's head upon the application of additional air pressure into the cylinder. Each bellows arrangement is provided within a cylinder for effecting displacement of the electrode. In essence, the bellows containing structure provides positive orientation control of the electrode independent of its displaced position.

Means are further provided for dispensing a predetermined amount of an electrolytic material from an external source of electrolyte, through the electrode, to the point of contact between the electrode and the subject's head.

BRIEF DESCRIPTION OF THE DRAWINGS

To the foregoing and still other objects and advantages of the present invention will be more apparent from the following detailed explanation of the preferred embodiments of the invention in connection with the accompanying drawings, wherein.

DESCRIPTION OF THE PREFFERED EMBODIMENTS

Figure 1:
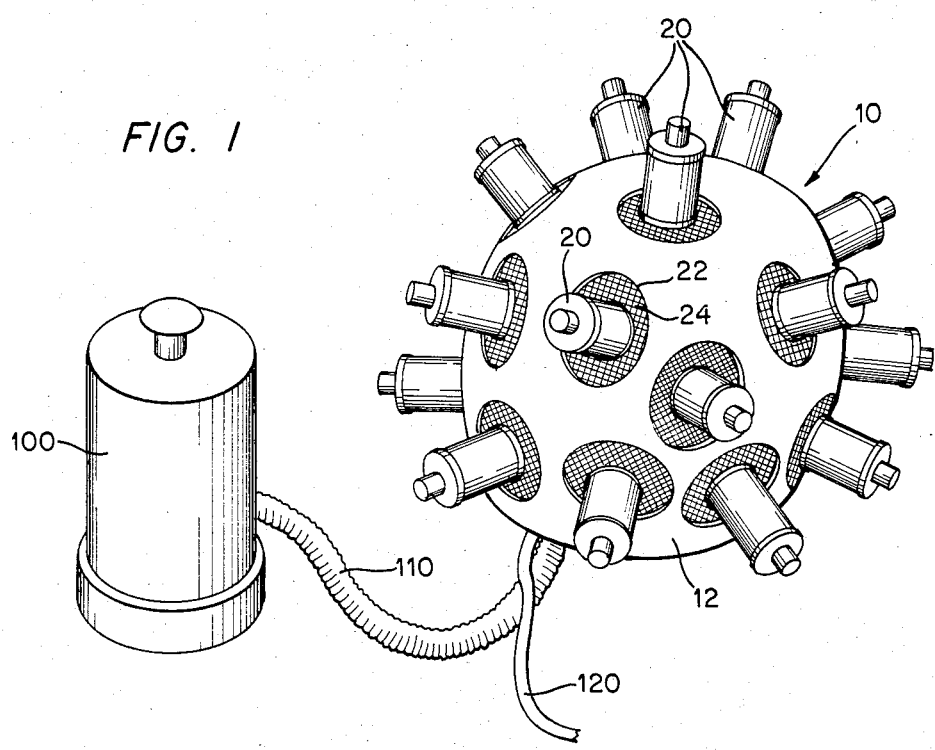
FIG. 1 is a perspective view of the headset of the present invention in combination with external means for adjusting the electrodes.
Figure 2:
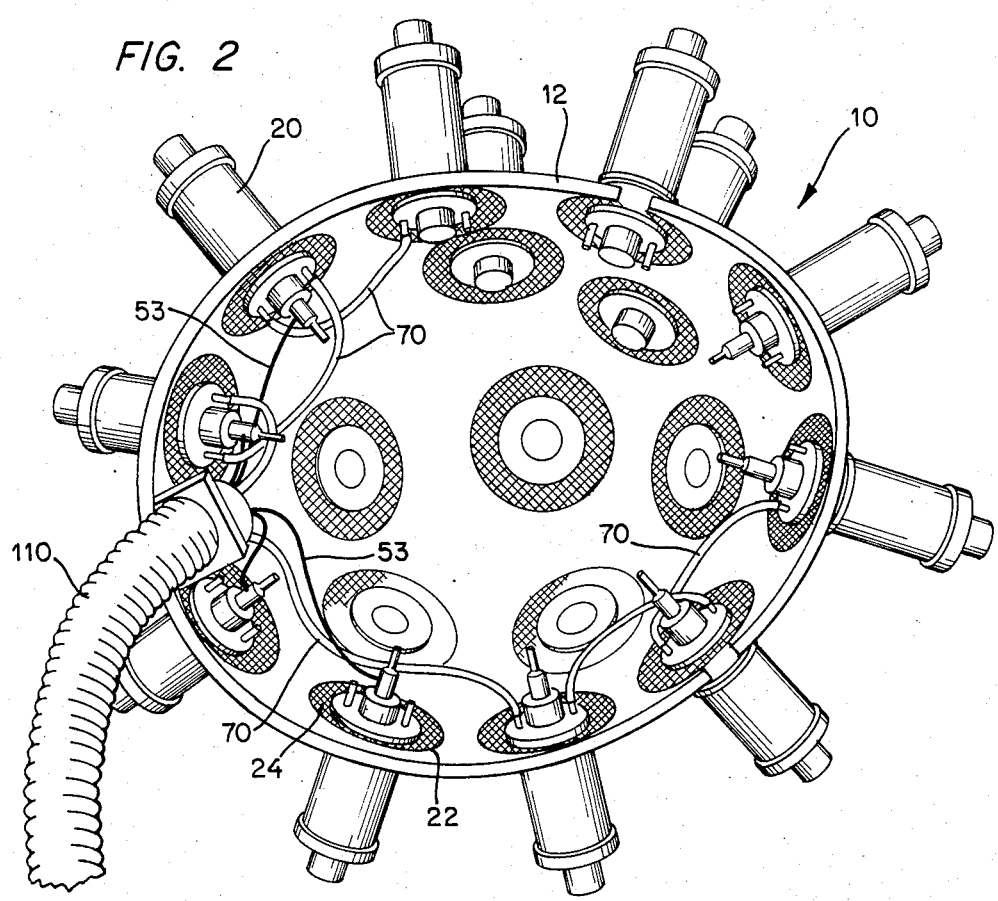
FIG. 2 is a bottom view of the headset of the present invention.

Referring now to drawings and, in particular, to FIGS. 1 and 2 thereof, the headset of the present invention includes a helmet liner 12 with a plurality of electrodes 20 placed at pre-determined positions about the liner 12. Liner 12 is preferably fabricated from a rigid, thermoplastic material and resembles a modified version of a hockey or football helmet.

A suspension system having a resilient, head-encircling headband (not shown) may be provided within the liner 12 to assist in orientation of the headset 10 on the subject being tested as well as to increase its comfort when worn for prolonged periods of time.

Nineteen electrodes 20 are provided at fixed locations about the headset 10 and are positioned in accordance with standard electroencephalographic procedures (International 10–20 System) for performing conventional EEG testing. In order to accommodate each of the electrodes 20, a like number of apertures 22 are provided in the liner 12 at the positions where the electrodes 20 are to be inserted. Each electrode 20 is retained within its respective aperture 22 by a resilient mesh 24 which encircles the electrode 20 and which may be adhesively bonded to the liner 12. By securing the electrode 20 within the aperture 22 by the use of the resilient mesh 24, the positioning of each electrode 20 is automatically adjusted to accommodate subjects having skulls of different sizes and shapes. The resilience of the mesh allows the technician to oscillate the electrode tip to displace the hair. Using an electrolyte gel, contact can be achieved with the scalp with only minimal pressure of the electrode 20 against the subject's scalp. An additional advantage of using a mesh 24 for resiliently securing the electrodes 20 is that it permits ventilating air through the liner 12 thus making the headset 10 more comfortable to wear for prolonged periods of time thereby avoiding problems arising from scalp perspiration which is conductive due to its salt content.

Alternatively, the resilient mesh 24 may be replaced with solid resilient material such as rubber, fabric or a thermoplastic material which would still provide the degree of resilience which the electrodes 20 require to position the electrodes as required by the International 10–20 System with respect to the subject's skull.*

*By arranging electrode travel perpendicular to the supporting shell, conformity of electrode placement to the 10–20 system is assured with variations of subject cranial size as perpendicular movement continues to arrange placement as fixed percentages of an individual's skull measurement as defined in the International 10–20 System.

It will be appreciated that the use of a liner 12 with predetermined apertures 22 which resiliently contain the electrodes 20 in predetermined positions about the liner 12 permit the electrodes 20 to be placed in substantially identical positions during repeated testing of the subject, thus insuring consistency of results in subsequent tests as well as of different sujects albeit the latter may have varying skull patterns and measurements.

Figure 3:
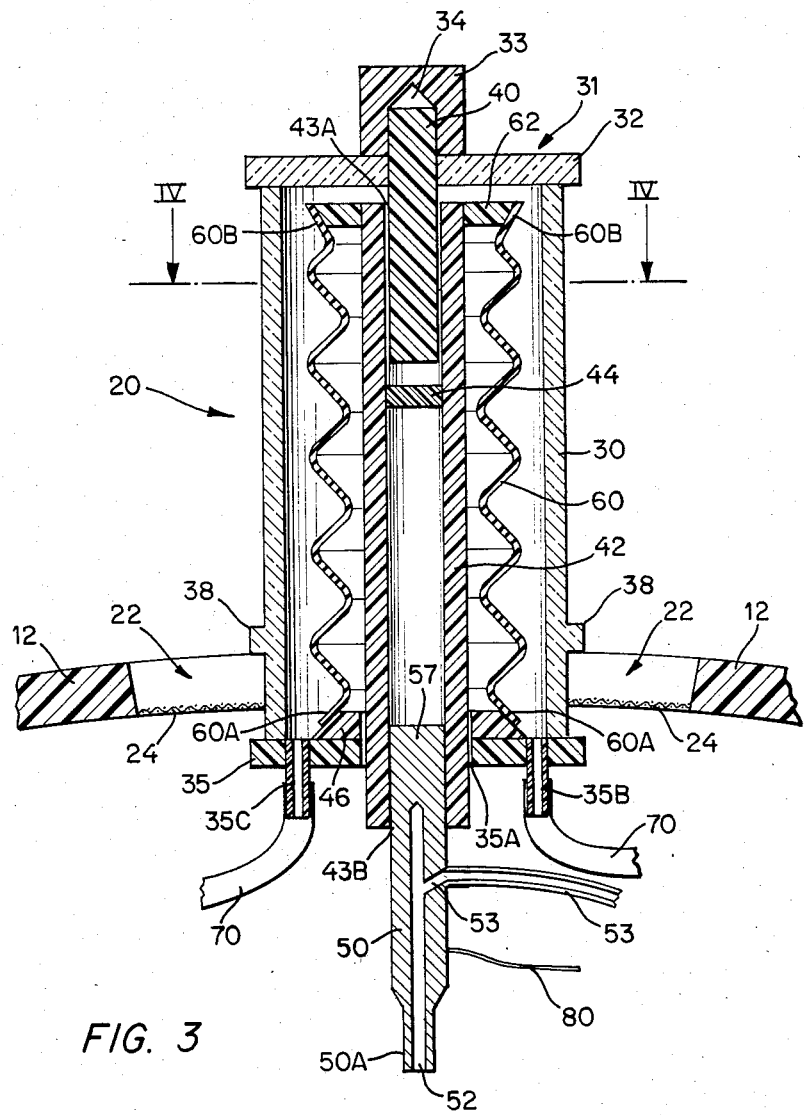
FIG. 3 is a sectional view of an electrode used in the headset of the present invention.
Figure 4:
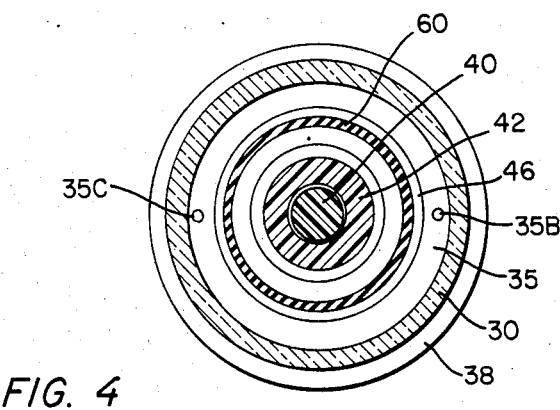
FIG. 4 is a sectional view taken along line IV—IV of FIG. 3.

The configuration of the electrodes 20 contained in the headset 10 is shown in greater detail in FIGS. 3 and 4. As shown in FIG. 3, the electrode 20 includes an outer cylinder 30 preferably fabricated from a clear thermoplastic material such as, for example, Lucite or a polystyrene. The cylinder 30 is adapted to be located within each aperture 22 of the liner 12 and is captured therein by resilient mesh 24 which adhesively bonded about the outer periphery of the cylinder 30 below a circular lip 38 which is provided about the outer periphery of the cylinder 30. The cylinder is sealed at its upper end 31 by an end cap 32 and a top cap 33 is provided in end cap 32. A center aperture 34 is provided through both the end cap 32 and the top cap 33. A post 40 is adhesively bonded to both the end cap 32 and the top cap 33 and extends downwardly into the interior of the cylinder 30. Loss of air pressure being supplied to any electrode results in the withdrawal of all of the electrodes and thus there is provided a fail safe system.

A hollow piston rod 42 having an upper end 43A and a lower end 43B and a center plug 44 is provided within the cylinder 30. Piston rod 42 is adhesively bonded about its outer periphery to bottom cap 35 which includes a center aperture 35A through which the piston rod 42 passes, as well as an air inlet 35B and an air outlet 35C. Bottom cap 35 integrally incorporates a shoulder 46 to effect a sealing plane for the bellows 60.

An electrode contact 50 is further provided having an upper end 51 adapted to engage the piston rod 42 and a lower end 50A adapted to contact the scalp of the subject being tested. The upper end 51 of the electrode contact 50 is captured within and bonded to the lower end 43B of the hollow piston rod 42. Thus, as the piston rod 42 travels within the cylinder, the electrode contact 50 will also travel a like amount toward the scalp of the subject.

A flexible, compressible bellows 60 is provided about the piston rod 42 within the cylinder 30. The bellows 60 is preferably constructed from synthetic or natural rubber, neoprene or high density polyethylene. Bellows 60 is adhesively bonded along its bottom edge 60A to shoulder 46 and is further bonded at its top edge 60B to top shoulder 62 which forms part of the piston rod 42. In this manner, the space between the bellows 60 and the piston rod 42 needs no additional sealing, i.e., it is open to the atmosphere enhancing freedom and movement of the electrode and therewith its positioning on the scalp. The bellows 60 arrangement within the cylinder 30 serves as a collapsible spring for moving the electrode tip assembly 50 toward and away from the subject's scalp to insure that proper pressure is maintained against the scalp during the EEG testing.

Movement of the piston rod 42 carrying the electrode assembly 50 is effected by controlling the amount of air pressure applied to the cylinder through the air inlet 35B from an external source of compressed air or other non-toxic gas (not shown) by air conduits 70 which are interconnected in such a manner that the air pressure is uniformly introduced into all of the air inlets 35B substantially simultaneously. As the air pressure within the cylinder 30 is increased, the bellows 60 compresses which causes the piston rod 42 to move downward toward the subject's scalp along with the electrode tip contact 50. Thus, by increasing the air pressure within the cylinder 30, the electrode tip contact 50 is moved toward teh subject's scalp and will thereby exert a uniform amount of pressure against the scalp in order to insure proper contact with the scalp to insure proper EEG readings.

Electrode tip contact 50, preferably fabricated from an electrically conductive material such as, for example, copper, includes a center aperture or residence cavity 52 which is open at the tapered open lower end 50A of the contact to permit the introduction of an electrolyte solution directly to the scalp of the subject through the lower end 50A. An inlet 53 is provided through the side of the contact 50, communicating with the center aperture 52 at one end and with a conduit 53 which is connected to an external source of electrolyte 100 (shown in FIG. 1) at its opposite end. As shown in FIGS. 1 and 2, the conduits 53 to each electrode tip contact 50 are gathered and fed through umbilical conduit 110 to the external source of electrolyte 100 thus permitting the substantially simultaneous introduction of electrolyte to all electrodes.

A particularly preferred electrolytic material is Electrode Gel, marketed by Parker Laboratories which is a buffered, non-corrosive electrolytic material. The Electrical Gel is diluted to permit passage through commercially available, non-corrosive, non-conductive tubing.

The electrode tip contacts 50 are also electrically connected in parallel by the use of electrically conductive copper leads 80 which are adapted to transmit the signal from the subject's brain wave to external instrumentation means (not shown) for monitoring and analyzing the signals and for generating the EEG results. The leads 80 from each contact 50 are gathered together and fed out of the headset 10 to the external instrumentation means through a contact umbilical conduit 120.

The operation of the headset 10 of the present invention is as follows. The headset 10 is placed on a subject's head. Due to the pre-fixed positioning of the electrodes 20 within the the headset, only minor adjustment is required to insure proper alignment. A chinstrap may be used, if desired to secure the headset 10 in place and to insure that it will be maintained in place during the testing. The electrode contacts 50 are then pressurized by the movement of the piston by air introduced into the air inlets 35B. Scalp contact will be held at a pressure of between about 1 and about 3 psi. As the bellows size is reduced, the pressure can be increased proportionately, the only limit being the subject's pain threshold. The electrolytic gel material is then introduced from the external electrolyte source through conduit 110 and pre-measured amounts of the material, typically between one and four drops, are then delivered to the center aperture 52 of each electrode contact 50, passing out of the open lower end 50A of the contact 50 to insure better electrical contact with the subject's scalp. The EEG test may then be run.

Having thus described the invention with particular reference to the preferred forms thereof, it will be obvious that various changes and modifications may be made therein without departing from the spirit and scope of the invention as defined by the appended claims.

Wherefore, we claim:

1. Apparatus for use in conjunction with an electroencephalographic (EEG) test, said apparatus comprising:
   a headset comprising a rigid helmet liner having an interior portion which is adapted to be accommodate the head of a subject to be EEG tested, said headset including a plurality of apertures provided at predetermined locations about said headset;

a plurality of electrodes, each of said electrodes being resiliently suspended in at least one of the apertures provided in said headset by the use of a resilient material provided within said aperture and secured to both the electrode and the headset; and means for displacing the electrodes in a direction toward the interior of said headset and means for holding the displaced electrodes in a fixed, displaced position so as to provide constant physical and electrical contact with the head of the subject in order that reliable EEG measurements may be taken.

2. The apparatus of claim 1 wherein said resilient material is selected from the group consisting of resilient fabric and plastic mesh.

3. The apparatus of claim 1 wherein said means for displacing the electrodes comprises an air cylinder for use in conjunction with each of said electrodes, each of said air cylinders being adapted to displace the electrode in a direction toward the interior of the headset.

4. The apparatus of claim 1 wherein each of said electrodes includes means for dispensing predetermined amounts of an electrically conductive material.

5. The apparatus of claim 4 wherein said electrically conductive material comprises an electrolytic material.

6. The apparatus of claim 1 wherein said resilient material is has means for permitting air to pass through said material in order to permit ventilation of the interior of the headset.

7. The apparatus of claim 1 wherein said resilient material is secured to the headset and to the electrode by an adhesive bond.

8. The apparatus of claim 1 wherein each of said said electrodes has means for connection to external monitoring means and are adapted to carry an electrical signal generated by the subject to said monitoring means for analysis thereof.

9. The apparatus of claim 1 wherein each of said electrodes are provided within an electrode retaining assembly including a fluid pressure operated reciprocating concentric bellows having a central opening adapted to receive and hold the electrode therein, and wherein said electrode is mounted in the central opening of said bellows.

10. The apparatus of claim 9 wherein said means for displacing the electrodes comprise means for applying fluid pressure to the bellows to thereby displace the electrode in a direction toward the interior of said headset.

11. The apparatus of claim 10 further including means for reducing the amount of fluid pressure applied to the bellows to permit retraction of the electrode from the interior of the headset.

12. The apparatus of claim 11 wherein said fluid pressure is air pressure.

13. The apparatus of claim 11 wherein said means for reducing comprises means for introducing compressed air into a cylinder in which said bellows are provided.

* * * * *